United States Patent
Clarke et al.

[11] Patent Number: 6,025,311
[45] Date of Patent: *Feb. 15, 2000

[54] FLUID SUSPENSION OF POLYSACCHARIDES FOR PERSONAL CARE AND HOUSEHOLD APPLICATIONS

[75] Inventors: Mary Theresa Clarke; Teng-Shau Young, both of Wilmington, Del.

[73] Assignee: Aqualon Company, Wilmington, Del.

[*] Notice: This patent is subject to a terminal disclaimer.

[21] Appl. No.: 08/168,895

[22] Filed: Dec. 17, 1993

[51] Int. Cl.[7] .............................. A61K 7/045; C11D 7/50; A01N 43/04; C08L 1/26

[52] U.S. Cl. .................... 510/121; 510/130; 510/135; 510/138; 510/159; 510/434; 510/471; 514/54; 514/57; 524/35; 106/176; 106/194; 106/197.1; 424/401; 424/70.13; 424/70.21; 424/70.22; 424/70.27; 424/70.31; 424/73; 424/78.09

[58] Field of Search .................................. 106/176, 194, 106/197.1; 252/174.17, 174.23, 174.25, 178, DIG. 2, 315.3; 510/121, 130, 135, 138, 159, 434, 471; 514/54, 57; 524/35

[56] References Cited

U.S. PATENT DOCUMENTS

| | | | |
|---|---|---|---|
| 4,069,062 | 1/1978 | Burge | 106/93 |
| 4,525,515 | 6/1985 | Peignier et al. | 106/170 |
| 5,028,263 | 7/1991 | Burdick | 106/194 |
| 5,228,908 | 7/1993 | Burdick et al. | 106/194 |
| 5,228,909 | 7/1993 | Burdick et al. | 106/194 |

*Primary Examiner*—M. L. Bell
*Assistant Examiner*—Patricia L. Hailey
*Attorney, Agent, or Firm*—David Edwards

[57] ABSTRACT

A stable fluid polymer suspension is composed of at least one water soluble polysaccharide polymer in an aqueous carrier fluid in which the polysaccharide polymer does not significantly swell or dissolve where the polysaccharide polymer in the aqueous carrier fluid has the measured properties of:

i) rendering the polymer(s) insoluble, resulting in a cloudy dispersion,
ii) limiting the swelling of insolubilized polymer(s), leading to a polymer sediment volume of a 1 weight percent polymer dispersion to less than 1%, and
iii) preventing phase separation for at least one week.

This invention also Includes a method of preparing the stable fluid polymer suspension having the above mentioned measured properties. The stable aqueous fluid suspension of this invention is a clear, odorless, and stable formulation and is used in cosmetics, personal care, and household products.

17 Claims, 4 Drawing Sheets

FLUID SUSPENSION OF POLYSACCHARIDES FOR PERSONAL CARE AND HOUSEHOLD APPLICATIONS

FIELD OF THE INVENTION

This invention relates to the use of aqueous fluid suspensions of polysaccharides in cosmetic, personal care and household applications.

BACKGROUND OF THE INVENTION

Prior to the present invention, processing difficulties were encountered when dispersing and incorporating dry polysaccharides, such as methylhydroxypropylcellulose (MHPC) and hydroxypropylcellulose (HPC), into water-containing liquid formulations using conventional methods of dispersion. It is well known that cellulosic polymers are widely used as thickening agents in aqueous based liquid formulations, such as liquid detergents, conditioners, shampoos, liquid hand soaps, and the like. Known prior art methods to overcome difficulties during dispersion of the dry MHPC into the formulation include: dispersion by heating the water to temperatures of 60–100° C.; dispersion by slurrying the cellulose ether in water miscible organic liquids such as alcohol or glycol; and dispersion by dry blending the cellulosic with powders. The disadvantages of these methods are the use of large amounts of energy in the form of heat, and long mixing cycles, and the presence of inflammable solvents, such as alcohol, which create the danger of a fire.

Still another difficulty encountered in the aforesaid dispersion methods is the formation of lumps of undissolved polysaccharide polymer in the aqueous medium which do not dissolve even after protracted periods of agitation (about 2–3 hours). This lumping problem requires an additional filtration step to rid the liquid formulation of said undissolved material. There is also a loss of thickening power when such undissolved material is filtered from the solution, which often requires re-work of the formulation.

Many prior art references exist that try to alleviate the above mentioned problems in the use of dry polysaccharide by using heated water and/or oil phases in order to disperse and dissolve the polymer prior to the addition to a formulation, such as for skin conditioning, detergents, shampoos, and the like. See U.S. Pat. Nos. 3,953,591, 3,549,542, 3,998,761, and 4,174,305.

Another approach for solving the above mentioned problems for incorporating polysaccharide polymers into household liquid formulations containing water is the use of a pre-mix of polymers dispersed in a water free liquified organic medium in which it does not swell or dissolve, prior to its incorporation into an aqueous formulation, using a short mixing cycle. This approach was described in U.S. Pat. No. 4,469,627.

None of the above prior art references discloses the incorporation into household and personal care products of a fluid polymer suspension system of polysaccharides. U.S. Pat. No. 4,883,536 discloses fluid polymer suspensions of cellulosic polymers using ammonium salts having multivalent anions that could be used in personal care products. An anonymous publication in a research disclosure in Derwent Week 1980-30 having a nominal publication date of Jul. 10, 1980 (publication DR 195006) is directed to a probable slurry of a cellulose ether comprising a methylcellulose derivative in an aqueous liquid with a sufficient amount of a water soluble salt of sodium carbonate or potassium carbonate to insolubilize the ether in the aqueous liquid. This anonymous publication does not suggest any potential use for this particular composition, nor does it give information enabling one to utilize these slurries in the present composition.

SUMMARY OF THE INVENTION

The present invention is directed to a composition comprising a stable fluid suspension of a water soluble polysaccharide in an aqueous carrier fluid in which the polysaccharide does not significantly swell or dissolve for use in preparing cosmetic, personal care, and household products. The aqueous carrier fluid of the instant invention is designed to:

(i) render the polymer(s) insoluble, resulting in a cloudy dispersion;

(ii) limit the swelling of the insolubilized polymer(s), leading to a polymer sediment volume of a 1 wt. % polymer dispersion of less than 15% as measured using a method described in Example 6; and (iii) prevent phase separation for at least one week.

This invention also comprehends a method for preparing an aqueous surfactant system used in formulating compositions for cosmetic, personal care and household products comprising a. preparing a stable fluid polymer suspension of a water soluble polysaccharide in an aqueous carrier fluid in which the polysaccharide does not significantly swell or dissolve, where the aqueous carrier fluid is designed to (i) render the polymer(s) insoluble, resulting in a cloudy dispersion;

(ii) limit the swelling of the insolubilized polymer(s), leading to a polymer sediment volume of a 1 wt. % polymer dispersion of less than 15%; and (iii) prevent phase separation for at least one week.

b. adding this fluid suspension to water or to a water-containing liquid formulation, and c. dissolving the fluid suspension therein by means of a short mixing cycle, whereby the resulting formulation is useful in cosmetic, personal care and household applications.

DETAILED DESCRIPTION OF THE INVENTION

This invention is concerned with the use of fluid aqueous suspensions of polysaccharides, selected from the methylhydroxypropylcellulose (MHPC), methylhydroxyethylcellulose (MHEC), methylcellulose (MC), hydroxyethylcellulose (HEC), hydrophobically modified hydroxyethylcellulose (HMHEC), or hydroxypropylcellulose (HPC) family, in cosmetic, personal care or household applications. In particular, this invention discloses the use of fluid suspensions of methylhydroxypropylcellulose (MHPC) as thickeners in surfactant systems, such as shampoos.

It has been found possible to prepare fluid, pumpable suspensions of MHPC, MHEC, MC, HEC, HMHEC and HPC which contain sufficiently high polymer solids and are useful in the preparation of cosmetic, personal care or household applications. Suspensions of this type, in general, comprise at least 10% by weight, preferably 20% by weight or higher, of a MHPC, MHEC, MC, HEC, HMHEC, or HPC in an aqueous liquid carrier. The aqueous liquid carrier contains dissolved or dispersed additives at sufficiently high concentrations to prevent the hydrophilic polysaccharide from swelling substantially or dissolving in the aqueous medium, thus rendering it fluid, and allows the polymer particles to be properly dispersed and suspended, thus providing the stability. Wherever necessary, small amounts, below 0.5% by weight, of preservative and/or surfactant are added to the composition to avoid microbial degradation and particle coagulation during storage. The resulting polymer suspension is typically fluid, pourable, and pumpable. Generally, the suspension has a viscosity of less than 7000 cP one day after preparation, as measured with a Brookfield Model LVT viscometer at 30 rpm. For easy pumping and mixing, a preferred product, with total polymer solids of 20% or higher, typically has a suspension viscosity of 3500 cP or less.

Figure 1:
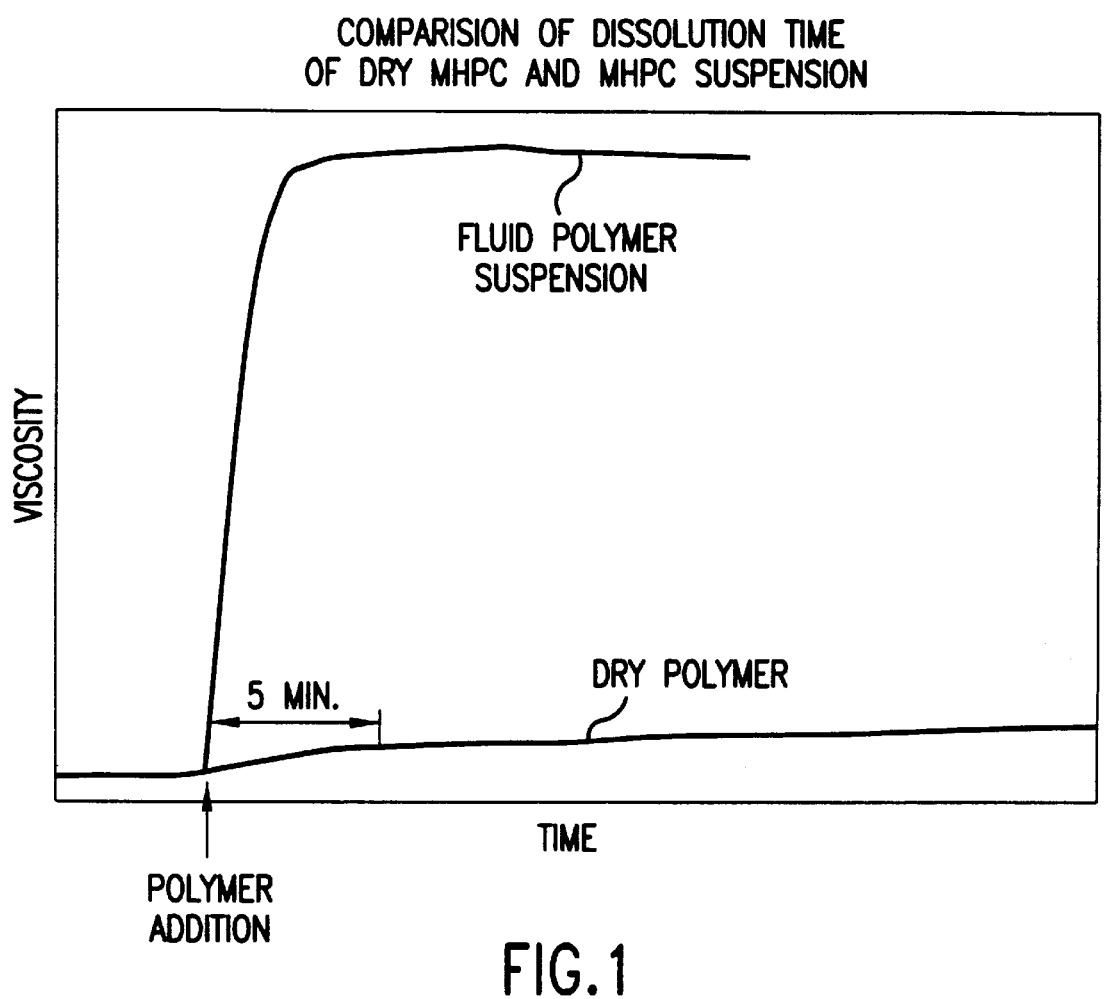
FIG. 1 is a comparison graph of the dissolution time of dry MHPC and a suspension.

When added to an aqueous system in the end application, such as a shampoo preparation, the suspension is diluted considerably and the concentration of the additives becomes so low that the polysaccharides will disperse and dissolve readily. In fact, the suspension can disperse and dissolve in aqueous media at a much higher rate than the dry polymer, since the polymer particles in the suspension have been pre-wetted and, in many cases, are slightly swollen. In other words, the instant invention allows a short mixing cycle of about 5–10 minutes rather than a 1 to 3 hour mixing period as required with dry ingredients as heretofore used. FIG. 1 illustrates the dissolution behavior, indicated by the viscosity development of the aqueous polymer solution, of a typical polymer suspension relative to its dry polymer counterpart at ambient temperature. The magnitude of increase in dissolution rate with the FPS is striking—it takes a typical FPS less than five minutes to develop more than 95% of the ultimate solution viscosity, while it takes the dry polymer more than 40 minutes under the same conditions. Dusting and particle lumping, two common problems in solution preparation of the dry polymer, are eliminated with the use of the fluid polymer suspension described by this invention.

The key to the preparation of a fluid suspension of this type is the limitation of swelling of the hydrophilic polymer in the aqueous medium. This may be achieved using one of several approaches which effectively reduce the solvating power of the aqueous carrier. A primary approach involves the addition of an inorganic salt; a wide variety of salts has been found useful for this purpose, if used properly. The concentration of salt must be adjusted such that the flocculation (or cloud) point, that is, the temperature at which a polymer precipitates or gels from solution to render a cloudy dispersion, is below room temperature. Examples 1 to 6 illustrate a few representative ways to prepare fluid MHPC, MHEC, and MC suspensions using an inorganic salt as the insolubilizing agent (IA).

EXAMPLE 1

Suspending MHPCs in Sodium Chloride Solution

Example 1 describes the preparation of MHPC suspensions using sodium chloride as the IA. Suspensions of two commercial MHPC products, BENECEL® MP943W, available from Aqualon, a Division of Hercules Incorporated, and Methocel® J75MS-N, available from Dow Chemical, were prepared as examples. Their compositions are given in Table 1. In the preparation process, a commercial xanthan gum, e.g., Kelzan® S from Kelco, was predissolved in water, which preferably was at a temperature of between 40 and 50° C., with vigorous agitation. Sodium chloride was then added under vigorous agitation to the warm xanthan gum solution and stirred until complete dissolution was achieved. The dry ground MHPC polymer powder is added gradually to the salt solution. The xanthan gum provided a structure to the polymer suspension, giving a yield value, which helped prevent settling of the polymer particles. At this point, a surfactant, if necessary, was added to the polymer slurry to help maintain long-term stability. A small amount of preservative was also added to provide bio-stability. These suspensions were nearly neutral, with pH values of 7.0±1.0. The suspensions were fluid and pourable, with a Brookfield viscosity of 3000 cP or less at 30 rpm. The Brookfield viscosity was measured approximately one day after preparation, unless specified otherwise. Both suspensions remained stable at ambient temperature for at least a month. In all the example formulations, ingredients are specified in parts by weight of the total formulation.

TABLE 1

Compositions of MHPC Suspensions Containing Sodium Chloride

|  | A | B |
|---|---|---|
| Water | 54.7 | 56.3 |
| MHPC, Aqualon BENECEL ® MP943W | 25.0 | — |
| MHPC, Dow Methocel ® J75MS-N | — | 24.5 |
| Sodium chloride | 20.0 | 18.7 |
| Xanthan gum, Kelzan ® S | 0.2 | 0.2 |
| Surfactant, Rhone-Poulenc Geropon ® TC-42 | — | 0.2 |
| Preservative, Methyl Parasept | 0.1 | — |
| Preservative, Glydant ® | — | 0.1 |

Viscosity (in M.Pa.s., or centipoise) was measured at varied shear rates (in rpm) with a Brookfield viscometer:

| rpm | A | B |
|---|---|---|
| 6 | 8400 | 5500 |
| 12 | 5350 | 3600 |
| 30 | 2960 | 2080 |
| 60 | 1910 | 1450 |

EXAMPLE 2

Preparation of MHEC and MC Suspensions

This example demonstrates the preparation of MHEC or MC suspensions using sodium chloride as the IA. These compositions, as shown in Table 2, are similar to those given in Table 1. They were prepared using the same procedure as described in Example 1.

TABLE 2

Compositions of MHEC and MC Suspensions Containing Sodium Chloride

|  | A | B |
|---|---|---|
| Water | 59.5 | 60.67 |
| MHPC, Aqualon Culminal ® 15000 PFF | 20.0 | — |
| MC, Aqualon Culminal ® 4000 PS | — | 20.0 |
| Sodium chloride | 20.0 | 19.0 |

TABLE 2-continued

Compositions of MHEC and MC Suspensions
Containing Sodium Chloride

|  | A | B |
|---|---|---|
| Xanthan gum, Kelzan ® S | 0.2 | 0.2 |
| Surfactant, Rhone-Poulenc Geropon ® TC-42 | 0.2 | — |
| Preservative, Methyl Parasept | — | 0.03 |
| Preservative, Glydant ® | 0.1 | — |
| Preservative, Germaben ® II | — | 0.1 |

Viscosity (in M.Pa.s., or centipoise) was measured at varied shear rates(in rpm) with a Brookfield viscometer (as above):

| rpm | A | B |
|---|---|---|
| 6 | 19000 | 6320 |
| 12 | 11750 | 3850 |
| 30 | 6040 | 2020 |
| 60 | 3740 | 1280 |

EXAMPLE 3

Preparation of MHPC Suspension Using Other Sodium Salts

This example illustrates the use of two other sodium salts, sodium citrate and sodium sulfate. Table 3 lists the compositions of the two sample suspensions. Again, they were prepared using the same procedure as that described in Example 1. The resulting suspensions also showed fluidity and stability for at least a month.

TABLE 3

Compositions of MHPC FPSs Containing
Sodium Citrate and Sodium Sulfate

|  | A | B |
|---|---|---|
| Water | 59.6 | 71.5 |
| MHPC, Aqualon BENECEL ® MP943W | 25.0 | 20.0 |
| Sodium citrate | 15.0 | — |
| Sodium sulfate | — | 8.0 |
| Xanthan gum, Kelzan ® S | 0.2 | 0.2 |
| Surfactant, Rhone-Poulenc Geropon ® TC-78 | 0.1 | 0.2 |
| Preservative, Methyl Parasept | — | 0.1 |
| Preservative, Glydant ® | 0.1 | — |

Viscosity (in M.Pa.s., or centipoise) was measured at varied shear rates (in rpm) with a Brookfield viscometer:

| rpm | A | B |
|---|---|---|
| 6 | 8400 | 10000 |
| 12 | 6650 | 6500 |
| 30 | 3900 | 3700 |
| 60 | 2650 | 2420 |

EXAMPLE 4

Preparing MHPC Suspension Using Potassium Chloride

This example illustrates the preparation of a MHPC suspension using potassium chloride as the IA.

TABLE 4

Composition of MHPC Suspension Containing KCl

|  | A |
|---|---|
| Water | 59.7 |
| MHPC, Aqualon BENECEL ® MP943W | 20.0 |
| Potassium chloride | 20.0 |
| Xanthan gum, Kelzan ® S | 0.2 |
| Preservative, Methyl Parasept | 0.05 |
| Preservative, Germaben ® II | 0.05 |

Viscosity (in M.Pa.s., or centipoise) was measured at varied shear rates (in rpm) with a Brookfield viscometer:

| rpm | A |
|---|---|
| 6 | 8400 |
| 12 | 5350 |
| 30 | 2960 |
| 60 | 1910 |

EXAMPLE 5

Preparing MHPC Suspensions Using Ammonium Salts

Ammonium salts such as diammonium phosphate and ammonium sulfate are also potent IAs. Table 5 shows two typical MHPC suspensions prepared using these ammonium salts.

TABLE 5

Compositions of Suspensions Comprising Ammonium Salts as IAs

|  | A | B |
|---|---|---|
| Water | 68.5 | 66.5 |
| MHPC, Aqualon Benecel ® MP943W | 20.0 | 23.0 |
| Diammonium phosphate | 11.0 | — |
| Ammonium sulfate | — | 10.0 |
| Xanthan gum, Kelzan ® S | 0.2 | 0.15 |
| Surfactant Rhone-Poulenc Geropon ® TC-78 | 0.2 | 0.2 |
| Preservative, Glydant ® | 0.1 | 0.05 |
| Preservative, Germaben ® II | — | 0.1 |

Viscosity (in M.Pa.s., or centipoise) was measured at varied shear rates (in rpm) with a Brookfield viscometer:

| rpm | A | B |
|---|---|---|
| 6 | 4100 | 9500 |
| 12 | 3000 | 5750 |
| 30 | 2020 | 3000 |
| 60 | 720 | 1950 |

A fluid suspension of MHPC or other MC derivatives may also be made using a combination of salts. Example 6 demonstrates the preparation of MHPC suspensions using a combination of sodium, potassium, and ammonium salts.

EXAMPLE 6

Preparing MHPC Suspensions Using Combinations of Salts

It has been found possible to prepare fluid suspensions of MHPC polymers using a combination of salts. The compositions shown in Table 6 demonstrate the use of combinations of sodium, potassium and ammonium salts as IAs. Suspensions prepared using this approach have been found to possess similar fluidity, stability, and dissolution characteristics to suspensions containing a single salt. This practice makes it possible to keep the concentration of particular salt anion(s) and/or cation(s) below certain limits in the end-use products, such as shampoos or lotions.

TABLE 6

Compositions of MHFC Suspensions Containing Mixed Salts

|  | A | B | C |
| --- | --- | --- | --- |
| Water | 59.75 | 62.75 | 62.75 |
| MHPC, Aqualon Benecel ® MP943W | 20.0 | 20.0 | 20.0 |
| Potassium chloride | 12.0 | — | 12.0 |
| Sodium chloride | 8.0 | 12.0 | — |
| Sodium sulfate | — | — | 5.0 |
| Diammonium phosphate | — | 5.0 | — |
| Xanthan gum, Kelzan ® S | 0.2 | 0.2 | 0.2 |
| Preservative, Methyl Parasept | 0.05 | 0.05 | 0.05 |

Viscosity (in M.Pa.s., or centipoise) was measured at varied shear rates (in rpm) with a Brookfield viscometer:

| rpm | A | B | C |
| --- | --- | --- | --- |
| 3 | 7600 | 17000 | 14000 |
| 20 | 1170 | 3600 | 3400 |
| 60 | 980 | 2300 | 2000 |

The above examples show that fluid polymer suspensions of the MC family polymers can be prepared using a wide variety of single or mixed salts. It was observed in this developmental work that for a salt to be effective, its concentration must be sufficiently high to render the polymer insoluble in the salt water at the temperature at which the fluid polymer suspension is to be stored and used. Furthermore, the salt concentration should be so high that swelling of the insolubilized polymer particles in the aqueous medium, if any, would occur only to a small degree. The above conditions are believed necessary to obtain a fluid MHPC, MC, MHEC, HEC, MHHEC or HPC suspension at a reasonably high polymer solids level.

Figure 2:
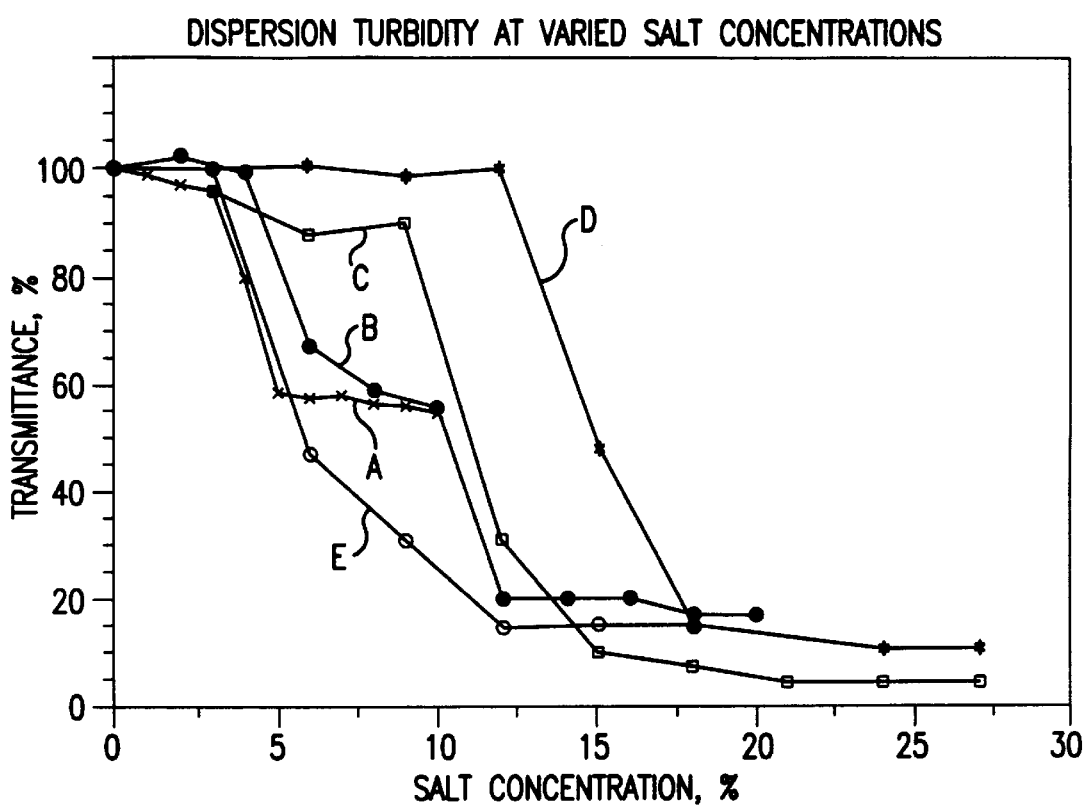
FIG. 2 is a comparison graph showing dispersion turbidity at varied salt concentrations.
Figure 3:
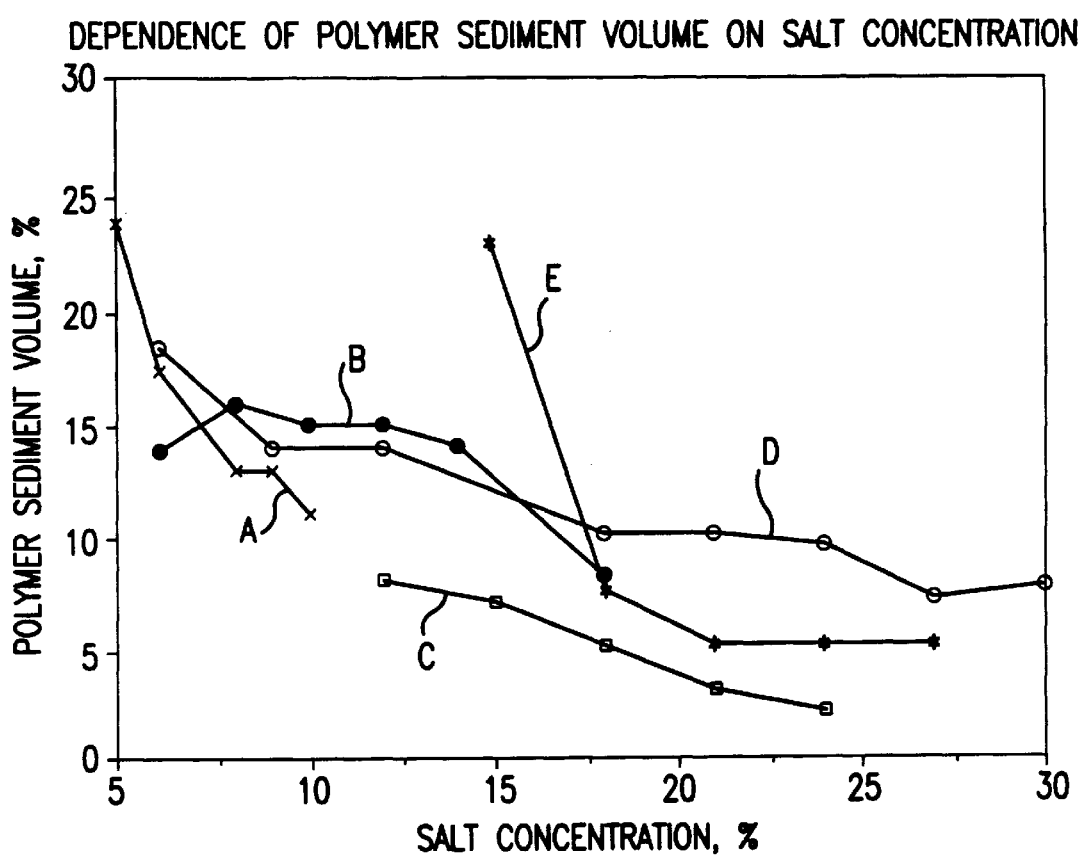
FIG. 3 is a comparison graph showing dependence of polymer sediment volume on salt concentration.

The following experiment was conducted to test this concept. In this experiment, a MHPC polymer was mixed into a series of salt solutions with increasing salt concentrations at ambient temperature to give a 1% aqueous dispersion. The MHPC polymer, Aqualon BENECEL® MP943W, is known to dissolve in water at ambient temperature, giving a solution with a Brookfield viscosity of about 300 cP. When added to solutions with a salt concentration higher than a certain threshold value in this experiment, this MHPC was insoluble and a cloudy dispersion resulted. Five different salts previously identified as useful IAs, sodium sulfate, sodium citrate, sodium chloride, potassium chloride, and diammonium phosphate (referred to as salts A, B, C, D, and E, respectively, in the FIGS. 2 and 3), were all found to render MHPC insoluble at ambient temperature at concentrations above specific threshold values. FIG. 2 shows the turbidity of the polymer dispersions for these five salts, which was expressed implicitly as % transmission of the dispersion, measured with a Bausch & Lomb Spectronic 20 turbidometer. As shown in the figure, threshold salt concentrations of 3 to 12 wt. % were observed for these salts. The turbidity of the polymer dispersion increased drastically at salt concentrations just above the threshold value and gradually leveled off at high salt concentrations. The onset of turbidity was accompanied by a sudden drop in dispersion viscosity. Above the threshold value, the dispersion viscosity was too low to be measured accurately with a Brookfield viscometer. However, the degree of swelling of the insoluble polymer particles continued to change with increased salt concentration. As shown in FIG. 3, the increase in dispersion turbidity (lower % of light transmitted) above the threshold value was associated with a reduction of polymer swelling, which was measured by the polymer sediment volume relative to the total dispersion volume observed after over-night settling. The continued decrease in the degree of polymer swelling is responsible for the reduction in dispersion viscosity, which renders it possible to obtain a suspension with reasonably high solids and yet good fluidity. For all of these salts, the operating suspension salt content was at least 5% higher than the threshold value, where polymer sediment volume approached a minimum. In this high concentration range, these salts caused dispersion transmittance values of below 55% and relative polymer sediment volumes of below 15%. It is thus contended that any salt which is effective as an IA—capable of delivering a suspension with at least 20% polymer solids—must fulfill two requirements: (1) be capable of showing a cloudy dispersion of the suspended polymer at a concentration below its solubility limit; and (2) be capable of limiting the relative polymer sediment volume, as measured using the procedure described above, to a value of below 15%. It is further contended that any salt or combination of salts may be used as an IA, so long as it satisfies these two conditions.

A fluid MHPC or HPC suspension may also be obtained using additives other than a single salt or mixed salts. It has been found that low molecular weight (MW) water soluble polymers and saccharides such as sugar are also alternative IAs. Their insolubilizing efficiencies are typically lower than some of the more efficient salts, and therefore often need to be used along with a salt. Examples 7 and 8 describe MHPC suspensions made with a combination of low molecular weight water soluble materials and salt.

EXAMPLE 7

Preparing MHPC Suspensions Using Salt and Low-MW CMC and HEC

Described herein are suspensions made with IAs that comprise a salt and a low-MW water soluble polymer, being a CMC or HEC. By adding the low-MW polymer, the salt requirement may be reduced. This feature may be useful in applications that have a low salt tolerance. AMBERGUM® 1570, a low-MW carboxymethylcellulose (CMC) supplied as a 15 wt. % aqueous solution, and AQU-D3137, a low-MW hydroxyethylcellulose (HEC) supplied as a 20 wt. % aqueous solution, both available from Aqualon, were used as the IA or co-IA in the compositions shown in Table 7. The resulting suspensions also displayed rapid dissolution in water and stability for at least one month.

TABLE 7

Compositions of Suspensions
Comprising Low-MW Cellulosic Polymers

|  | A | B | C |
|---|---|---|---|
| Water | 68.13 | 70.65 | 73.1 |
| MHPC, Aqualon Benecel ® MP943W | 20.0 | 15.0 | 15.0 |
| Low-MW CMC, as in AMBERGUM ® 1570 | — | — | 8.0 |
| Low-MW HEC, as in AQU-D3137 | 5.0 | 10.0 | — |
| Sodium sulfate | 6.5 | 4.0 | — |
| Sodium carbonate | — | — | 3.4 |
| Xanthan gum, Kelzan ® S | 0.1 | 0.1 | 0.2 |
| Surfactant, Rhone-Poulenc Geropon ® AC-78 | 0.1 | 0.1 | 0.1 |
| Surfactant, Rhone-Poulenc Geropon ® AS-200 | — | — | 0.1 |
| Preservative, Methyl Parasept | 0.07 | 0.05 | — |
| Preservative, Glydant ® | 0.1 | 0.1 | — |
| Preservative, Germaben ® II | — | — | 0.1 |

Viscosity (in M.Pa.s., or centipoise)was measured at varied shear rates (in rpm) of a Brookfield viscometer:

| rpm | A | B | C |
|---|---|---|---|
| 6 | 9000 | 10500 | 14000 |
| 12 | 5250 | 8150 | 10000 |
| 30 | 3700 | 6800 | 6700 |
| 60 | 2950 | 5640 | 4880 |

EXAMPLE 8

Preparing a MHPC Suspension Using a Sugar/Salt Mixture

It was found that low-MW saccharides such as sugar, which has good water affinity, may also help insolubilize the MHPC family polymers. As an example, the composition given in Table 8 teaches the use of a mixture of sugar and sodium sulfate as the IAs. With the presence of sugar, the amount of salt required is reduced. Thus, saccharides such as sugar appear to function in a way similar to the low MW water-soluble polymers described above.

TABLE 8

Suspension Comprising Sugar as a Co-IA

| Ingredient | A |
|---|---|
| Water | 44.85 |
| Sugar, food grade | 30.0 |
| Sodium Sulfate | 5.0 |
| MHPC, BENECEL ® MP943W | 20.0 |
| Hercules ® DF 285 Defoamer | 0.1 |
| Preservative, Proxel CRL | 0.05 |

Viscosity (in M.Pa.s., or centipoise) was measured at varied shear rates (in rpm) with a Brookfield viscometer:

| rpm | A |
|---|---|
| 6 | 1000 |
| 12 | 750 |
| 30 | 560 |

EXAMPLE 9

Preparing HPC Suspensions Using Salt and Low-MW Polymer/Salt Mixture

It has been found that the same approaches used to prepare MHPC suspensions also apply to HPC, which is a less hydrophilic polymer than MHPC. Therefore, a smaller amount of IA(s) is used in the preparation of a HPC suspension. Table 9 shows the compositions of two typical HPC suspensions, using a single salt and a mixture of salt/low-MW HEC as the IA, respectively. The resulting suspensions showed dissolution times in water of less than 10 minutes. This is substantially shorter than that of the dry HPC product, which is typically longer than 45 minutes at ambient temperature.

TABLE 9

Compositions of HPC Suspensions

| Ingredient | A | B |
|---|---|---|
| Water | 71.63 | 75.63 |
| HPC, KLUCEL ® HXF | 20.0 | 20.0 |
| Low-MW HEC (as in AQU-D3137) | 5.0 | — |
| Sodium sulfate | 3.0 | 4.0 |
| Xanthan gum, Kelzan S | 0.2 | 0.2 |
| Hercules ® DF 285 defoamer | 0.1 | 0.1 |
| Preservative, Methyl Parasept | 0.07 | 0.07 |
| Brookfield Viscosity at 30 rpm - 13 days old | 3160 | 2340 |

EXAMPLE 10

Suspending HEC and Hydrophobically Modified HEC

The concept of fluidizing dry polysaccharides for improved manufacturing operation and enhanced performance in cosmetic, personal care and household uses also applies to hydroxyethylcellulose (HEC) and hydrophobially modified HEC (HMHEC) polymers. This example describes the preparation of FPS compositions comprising an HEC (Natrosol® 250HX, NF grade, available from Aqualon) or HMHEC (PolySurf® 67, also available from Aqualon). Both suspensions remained stable and fluid for more than two months after preparation.

TABLE 10

Suspensions Comprising HEC and HMHEC

| Ingredient | A | B |
|---|---|---|
| Water | 59.5 | 62.65 |
| PolySurf ® 67 hydrophobically modified hydroxyethylcellulose | 22.7 | — |
| Natrosol ® 250HX HEC, NF Grade | — | 20.0 |
| Diammonium Phosphate | 17.5 | — |
| Diammonium Sulfate | — | 17.0 |
| Xanthan Gum, Kelzan ® S | 0.2 | 0.25 |
| Preservative, Methyl Parasept | 0.1 | — |
| Preservative, Glydant ® | — | 0.1 |
| Brookfield Viscosity at varied rpm | | |
| 6 | 6600 | 7400 |
| 12 | 4050 | 4700 |
| 30 | 2720 | 2600 |
| 60 | 2050 | 1720 |

EXAMPLE 11

Suspension Compositions Comprising More Than One Polysaccharide

The FPS compositions of this invention can comprise more than one polysaccharide, with a total polysaccharide content of at least 20 wt. %. For example, Compositions A and B in Table 11 are fluid suspensions of MHPC/HPC and MHPC/HEC mixtures respectively.

TABLE 11

Suspensions Comprising More Than One Polysaccharide

| Ingredient | A | B |
|---|---|---|
| Water | 69.7 | 62.65 |
| Xanthan Gum, Kelzan ® S | 0.2 | 0.25 |
| Sodium Sulfate | 8.0 | — |
| Diammonium Sulfate | — | 17.0 |
| MHPC, Benecel ® 943 W | 11.0 | 10.0 |
| HPC, Klucel ® HXF | 11.0 | — |
| HEC, Natrosol ® 250HX, NF Grade | — | 10.0 |
| Preservative, Glydant ® | 0.1 | 0.1 |
| Brookfield Viscosity at varied rpm | | |
| 6 | 8000 | 6360 |
| 12 | 4750 | 3960 |
| 30 | 2680 | 2220 |
| 60 | 1650 | 1460 |

The performance advantages of suspension compositions cited in this invention, when used in cosmetic, personal care and household products, include, but are not limited to, significantly reduced polymer dissolution time, ease of thickener addition and handling, ability to add thickener at any point during the manufacturing process, elimination of lumping associated with dry thickeners, and ability to post-adjust finished product viscosity.

Additional and unexpected benefits for selected compositions include improved viscosity synergism and enhanced lather quality, versus dry added thickener, as observed in finished shampoo formulations, shown in Examples 12 and 13, respectively. Unexpected viscosity boost in aqueous surfactant solutions is demonstrated in Example 14. Selected suspension compositions, including the preferred compositions, have the important unexpected benefits of not adversely affecting finished formulation appearance, in terms of clarity and color, or odor. This is critical in cosmetic, personal care and household products, where formulation aesthetics play an important role in consumer acceptability. This is particularly evident in household and personal care products marketed as being clear in appearance.

All suspension compositions cited in this invention, in addition to possessing the properties described earlier in this text, have been carefully formulated to contain ingredients that are generally recognized as acceptable for use in cosmetic and personal care applications. Preferred compositions contain ingredients cited in the CTFA International Cosmetic Ingredient Dictionary, 4th Edition.

EXAMPLE 12

Performance of Fluid Polymer Suspensions in Shampoo Formulation

Example 12 describes the use of typical fluid polymer suspensions cited in this invention in a shampoo formulation. Performance comparisons are made with a control shampoo without added polymeric thickener and a shampoo containing dry-added polymer. This example demonstrates benefits of the suspensions in surfactant-based formulations, including manufacturing flexibility and significant manufacturing time savings. Use of dry polymer requires an added manufacturing step, heating ⅓ of the formulation water to above 55° C. for the purpose of facilitating polymer dispersion and eliminating lumping. The fluid suspensions were added at the end of the shampoo batch, allowing for post-manufacturing viscosity adjustment. Compared to dry added Benecel® MP943W MHPC, suspension compositions based on this same polymer, as described in Tables 1 and 4, yield an unexpected viscosity boost in shampoo formulation A.

Shampoo Formulation A

| Ingredient | Brand | Concentration |
|---|---|---|
| Water | | q.s. to 100.00 |
| Ammonium Lauryl Sulfate | Stepanol AM | 27.50 |
| Cocoamphodiacetate | Miranol C2M Conc NP | 6.90 |
| Sodium Laureth Sulfate | Steol CS-460 | 5.70 |
| Thickener | see Table 12 | see Table 12 |
| DMDM Hydantoin | Glydant | 0.30 |
| Methyl Paraben | Methyl Parasept | 0.10 |
| Citric Acid | | to pH 5.5 |

Shampoo base appearance: Clear, colorless

Table 12 presents evaluation results, demonstrating a significant reduction in batch time and unexpected improved viscosity build by use of fluid polymer suspensions, versus dry-added MHPC.

TABLE 12

Performance of HMPC Fluid Suspension in Shampoo Formulation

| Thickener | None | Benecel ® MP943W Dry | MHPC suspension | MHPC suspension | MHPC suspension | MHPC suspension. |
|---|---|---|---|---|---|---|
| Suspension Composition from Table Reference | — | — | 1A | 1B | 2A | 4A |
| Use Level (wt %) Wet Basis | 0 | n/a | 1.44 | 1.47 | 1.80 | 1.8 |
| Dry Polymer Basis | 0 | 0.36 | 0.36 | 0.36 | 0.36 | 0.36 |
| Total Batch Time (Minutes) | 32 | 52 | 35 | 38 | 38 | 35 |
| Shampoo Brookfield Viscosity (LVT, 30 rpm, 25° C.) in cps | | | | | | |
| 24 hours | 555 | 4170 | 6410 | 8920 | 5710 | 5180 |
| 2 weeks | 500 | 3910 | 5180 | 6950 | 4510 | 5540 |

EXAMPLE 13

Influence of Polymer Suspensions on Lather Quality of Surfactants

MHPC is used in surfactant formulations, particularly in shampoos, for its ability to stabilize lather, in addition to performance as a thickener. Addition of other formulation ingredients can have an adverse affect on lather quality, a critical aspect of product performance. Thus, it is important that the suspension composition (does) not adversely affect the polymer's lather stabilization ability, as demonstrated in this example. In certain cases, lather quality may be improved. Lather quality is determined using a drainage time test, published in the literature: J. R. Hart and M. T. DeGeorge, "The Lathering Potential of Surfactants—A Simplified Approach to Measurement", *J. Soc. Cosm. Chem.*, 31, 223–236 (1980). High lather drainage times indicate improved lather quality. As in Example 12, the dry polymer is hydrated at the beginning of the batch, prior to addition of other ingredients. The MHPC suspensions are added at the end of the shampoo batch.

Table 13 presents results of a shampoo lather drainage test, as described above. MHPC in fluid suspension form performed equal to or better than dry-added MHPC at an equivalent dry polymer addition level.

TABLE 13

Influence of Fluid Polymer Suspensions on Shampoo Lather Quality
Test Formulation - Shampoo Formulation A (see Example 12)

| Thickener | None | Benecel ® MP943W Dry | MHPC suspension | MHPC suspension |
|---|---|---|---|---|
| Suspension Composition From Table Reference | — | — | 7A | 7B |
| Use Level (wt %) | | | | |
| Wet Basis | 0 | N/A | 1.80 | 2.40 |
| Dry Polymer Basis | 0 | 0.36 | 0.36 | 0.36 |
| Lather Drainage Time (sec) at 25° C. | 56.7 ± 0.6 | 63.0 ± 1.0 | 64.7 ± 1.1 | 63.7 ± 0.6 |

EXAMPLE 14

Viscosity Synergy of Polymer Suspension in Surfactants

Figure 4:
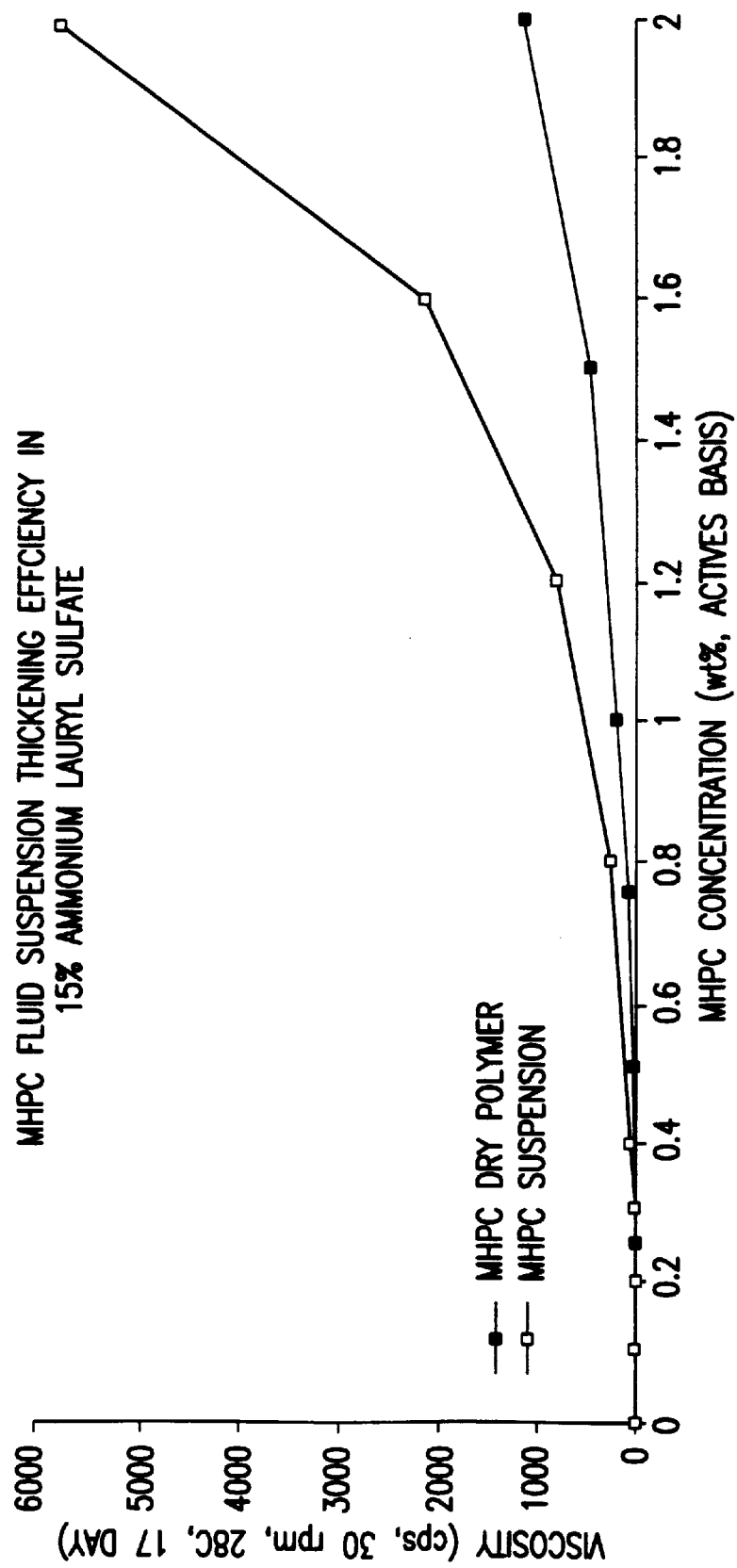
FIG. 4 is a graph showing MHPC fluid suspension thickening efficiency in 15% ammonium lauryl sulfate.

Fluid polymer suspensions cited in this invention have demonstrated an unexpected viscosity boost in selected surfactant systems. Viscosities observed are greater than the sum of anticipated contributions of individual suspension ingredients. This example illustrates an observed viscosity boost in a 15 wt % actives ammonium lauryl sulfate solution. At a polymer actives level of 2.0 wt %, the viscosity achieved is greater than 5 times that using dry added MHPC. FIG. 4 shows a graph of MHPC fluid suspension thickening efficiency in 15% ammonium lauryl sulfate.

EXAMPLE 15

Utility of Fluid Polymer Suspensions in Hair Conditioners

Fluid polymer suspensions of hydroxyethylcellulose can be used in hair conditioner products, in place of dry-added HEC. This example in Table 15 typifies an oil-in-water emulsion hair conditioner. The HEC fluid suspension contributes viscosity build, emulsion stability and lubricious feel.

TABLE 15

Cream Rinse Hair Conditioner with HEC Fluid Suspension

| Ingredient | Brand | Concentration |
|---|---|---|
| Water | — | q.s. to 100.00 |
| Stearalkonium Chloride | Varisoft SDC | 10.0 |
| HEC Suspension Composition From Example 10B | — | 7.5 |
| Polyquaternium-17 | Mirapol AD-1 | 1.8 |
| Propylene Glycol | BASF | 1.5 |
| Glycol Stearate | Cyclochem EGMS | 1.5 |
| Oleth-20 | Emulphor ON-870 | 1.5 |
| Fragrance | — | 0.2 |
| Methylchloroisothiazolinone and Methylisothiazolinone | Kathon CG | 0.08 |

EXAMPLE 16

Utility of Fluid Polymer Suspensions in Bubble Bath Products

The bath gel formulation illustrated in Table 16 is based on an fluid suspension version of hydroxypropylcellulose used in place of dry-added HPC. The HPC fluid suspension functions as a viscosifier.

TABLE 16

Bath Gel with HPC Fluid Suspension

| Ingredient | Brand | Concentration |
|---|---|---|
| Water | — | q.s. to 100.00 |
| TEA-Lauryl Sulfate | Stepanol WAT | 20.0 |
| HPC Fluid Suspension Composition From Example 9B | — | 5.0 |
| Lauramide DEA | Monamid 716 | 4.0 |
| PPG-20 Lanolin Ether | Solulan PB-20 | 1.0 |
| Fragrance | — | 0.2 |
| Methylchloroisothiazolinone and Methylisothiazolinone | Kathon CG | 0.08 |

EXAMPLE 17

Utility of Fluid Polymer Suspensions in Lotions

Lotion products can be formulated using fluid polymer suspensions of hydrophobically modified hydroxyethylcellulose (HMHEC) instead of dry-added HMHEC. The lotion in Example 17 utilizes PolySurf® 67 HMHEC in fluid suspension form to provide viscosity build with pseudoplastic flow.

TABLE 17

Oil-In-Water Lotion Based on HMHEC Fluid Suspension

| Ingredient | Brand | Concentration |
|---|---|---|
| Water | — | q.s. to 100.00 |
| Glycol Stearate | Cyclochem EGMS | 2.75 |
| HMHEC Suspension Composition From Example 10A | — | 2.20 |
| Glycerin | Superol | 2.00 |
| Mineral Oil | Drakeol 9 | 2.00 |
| Propylene Glycol and Diazolidinyl Urea and Methylparaben and Propylparaben | Germaben II | 0.75 |

TABLE 17-continued

Oil-In-Water Lotion Based on HMHEC Fluid Suspension

| Ingredient | Brand | Concentration |
|---|---|---|
| Triethanola mine | Dow | 0.50 |
| Acetylated Lanolin | Ritacetyl | 0.50 |
| Cetyl Alcohol | Adol 52N | 0.25 |

EXAMPLE 18

Utility of Fluid Polymer Suspensions in Light Duty Detergents

The light duty dishwashing liquid formulation in Table 18 is based on a fluid polymer suspension form of HEC. The HEC fluid suspension acts as a viscosifying agent in this product.

TABLE 18

Dishwashing Liquid Based on HEC Fluid Suspension

| Ingredient | Brand | Concentration |
|---|---|---|
| Water | — | q.s. to 100.00 |
| Sodium Alkylbenzene Sulfonate | C-550 slurry | 13.6 |
| Linear C10–C12 Alcohol Ethoxylate | Alfonic 1012-60 | 13.1 |
| HEC Suspension Composition from Table 10B | — | 6.0 |
| Propylene Glycol and Diazolidinyl Urea and Methylparaben and Propylparaben | Germaben II | 0.7 |
| Fragrance | — | 0.2 |

What is claimed is:

1. A cosmetic, personal care, or household product composition using a fluid polymer suspension comprising in admixture at least one cosmetic, personal care, or household ingredient and a stable fluid suspension of at least one water soluble polysaccharide polymer selected from the group consisting of methylhydroxypropylcellulose, methylhydroxyethylcellulose, methylcellulose, hydroxypropylcellulose, or hydrophobically modified hydroxyethylcellulose in an aqueous carrier fluid comprising an aqueous solution of at least one salt in which the polysaccharide polymer does not significantly swell or dissolve where the aqueous carrier fluid has the measured properties of:
    i) rendering the polymer(s) insoluble, resulting in a cloudy dispersion,
    ii) limiting the swelling of insolubilized polymer(s), leading to a polymer sediment volume of a 1 weight percent polymer dispersion to less than 15%, and
    iii) preventing phase separation for at least one week.
2. The composition of claim 1 wherein the aqueous carrier fluid is a solution of at least one low molecular weight water soluble polymer.
3. The composition of claim 1 wherein the carrier fluid contains at least one mono- or disaccharide.
4. The composition of claim 1 wherein the carrier fluid contains at least two members selected from the group consisting of at least one salt, at least one low molecular weight water soluble polymer and at least one mono- or disaccharide.
5. The composition of claim 1 wherein the at least one cosmetic ingredient is a lotion formulation.
6. The composition of claim 1 wherein the at least one household product ingredient is a detergent formulation.
7. The composition of claim 1 wherein the at least one personal care ingredient is selected from the group consisting of a shampoo, bubble bath, hair conditioner and hand soap formulation.
8. The composition of claim 1, wherein xanthan gum is present.
9. The composition of claim 8, wherein at least one preservative and at least one surfactant are present.
10. The composition of claim 1, wherein the at least one salt is selected from the group consisting of sodium chloride, potassium chloride, and sodium citrate.
11. A method for preparing a cosmetic, personal care, and household product composition using an aqueous surfactant system comprising:
    a) preparing a stable fluid polymer suspension of a water soluble polysaccharide selected from the group consisting of methylhydroxypropylcellulose, methylhydroxyethylcellulose, methylcellulose, hydroxypropylcellulose or hydrophobically modified hydroxyethylcellulose in an aqueous carrier fluid comprising an aqueous solution of at least one salt in which the polysaccharide does not significantly swell or dissolve where the aqueous carrier fluid has the measured properties of:
        i) rendering the polymer(s) insoluble, resulting in a cloudy dispersion,
        ii) limiting the swelling of insolubilized polymer, leading to a polymer sediment volume of a 1 weight percent polymer dispersion of less than 15%, and
        iii) preventing phase separation for at least one week,
    b) adding this fluid suspension to water or to a water-containing liquid cosmetic, personal care, or household product formulation, and
    c) dissolving the fluid suspension therein by means of a short mixing cycle, whereby the resulting formulation is (i) a component of a cosmetic, personal care or household product that is added to a cosmetic, personal care, or household product formulation or (ii) a cosmetic, personal care, or household product.
12. The method of claim 11 wherein the aqueous carrier fluid is a solution of at least Onto low molecular weight water soluble polymer.
13. The method of claim 11 wherein the carrier fluid contains at least one mono- or disaccharide.
14. The method of claim 11 wherein the carrier fluid contains at least two members selected from the group consisting of at least one salt, at least one low molecular weight water soluble polymer and at least one mono- or disaccharide.
15. The method of claim 11 wherein the resulting formulation is a clear, colorless, and stable formulation.
16. The product prepared by the method of claim 11.
17. The composition of claim 11, wherein the at least one salt is selected from the group consisting of sodium chloride, potassium chloride, and sodium citrate.

* * * * *